US008097074B2

(12) United States Patent
Helvenston et al.

(10) Patent No.: US 8,097,074 B2

(45) Date of Patent: Jan. 17, 2012

(54) AIR FILTRATION AND ABSORPTION METHOD AND SYSTEM FOR THE REMEDIATION OF HYDRAZINE

(75) Inventors: Merritt C. Helvenston, Las Vegas, NM (US); Rodolfo A. Martinez, Santa Fe, NM (US); Jose C' De Baca, Las Vegas, NM (US); John R. Juarez, Albuquerque, NM (US)

(73) Assignee: New Mexico Highlands University, Las Vegas, NM (US)

( * ) Notice: Subject to any disclaimer, the term of this patent is extended or adjusted under 35 U.S.C. 154(b) by 374 days.

(21) Appl. No.: 12/504,917

(22) Filed: Jul. 17, 2009

(65) Prior Publication Data

US 2011/0011266 A1 Jan. 20, 2011

(51) Int. Cl.
*C07C 243/10* (2006.01)
*B01D 53/14* (2006.01)

(52) U.S. Cl. .......................... 96/296; 423/235; 422/122

(58) Field of Classification Search .............. 95/90, 128, 95/232; 96/108, 243, 297; 423/235, 236, 423/239.1; 588/300, 313, 315, 400, 403, 588/410; 422/120, 122, 129

See application file for complete search history.

(56) References Cited

U.S. PATENT DOCUMENTS

| | | | |
|---|---|---|---|
| 4,804,527 A | 2/1989 | Tatarchuk et al. | |
| 4,877,425 A * | 10/1989 | Norman et al. | 95/172 |
| 6,107,523 A * | 8/2000 | Virnig et al. | 568/412 |
| 7,074,959 B2 | 7/2006 | Helvenston et al. | |
| 7,345,015 B1 | 3/2008 | Kong et al. | |
| 2004/0024251 A1 | 2/2004 | Helvenston et al. | |
| 2005/0121054 A1 | 6/2005 | Barnabas et al. | |
| 2008/0134893 A1* | 6/2008 | Kuo et al. | 95/274 |
| 2009/0101589 A1 | 4/2009 | Lee | |
| 2011/0182780 A1* | 7/2011 | Martinez et al. | 422/198 |

* cited by examiner

*Primary Examiner* — Frank Lawrence, Jr.

(74) *Attorney, Agent, or Firm* — Kermit D. Lopez; Luis M. Ortiz; Ortiz & Lopez, PLLC

(57) ABSTRACT

An air filtration system and method for the remediation of hydrazine from contaminated air. The system is provided in the form of a container with an inlet port and an outlet port containing absorbent pads or filters or wipes saturated with a solution of a dicarbonyl compound. As contaminated air passes through the container, hydrazine present within the air reacts with the dicarbonyl compound and becomes neutralized, thereby resulting in the exit of pure air from the container. The absorbent pads can also be used independently to remove hydrazine liquid spill.

35 Claims, 8 Drawing Sheets

10

2-Ketoglutaric acid (2KGA)

6-Oxo-1,4,5,6-Tetrahydropyridazine-3-Carboxylic acid

20

2-Ketoglutaric acid (2KGA)

6-Oxo-1,4,5,6-Tetrahydro-1-Methyl-Pyridazine-3-Carboxylic acid (MePCA)

25

I

27

II

29

III

31

IV

R = H, alkyl or aryl, and A = O, N, or other heteroatom

60

70

D,L-Proline, 5-oxo-
"D,L-pyroglutamic acid"

AIR FILTRATION AND ABSORPTION METHOD AND SYSTEM FOR THE REMEDIATION OF HYDRAZINE

TECHNICAL FIELD

Embodiments are related to an air filtration system and more particularly to a method and system for the remediation of hydrazine, 1,1-dimethylhydrazine, and/or monomethyl-hydrazine from contaminated air. Embodiments are also related to absorbent materials, aerosols, and/or dry powders for the removal of hydrazine, 1,1-dimethyhydrazine, and/or monomethyl-hydrazine from contaminated air.

BACKGROUND OF THE INVENTION

Numerous industries utilize hydrazine on a daily basis. Highly toxic hydrazine fuels, for example, are respectively utilized by the United States Air Force and NASA as an emergency power source on the F-16 and as rocket propellant. The civilian industry also requires hydrazine in the manufacture of agricultural chemicals and pharmaceuticals, in photography, and also, for example, as an oxygen scavenger to prevent corrosion in boilers. Additionally, large volumes of such fuels are shipped across the highways and rail systems annually, increasing the probability of an accidental spill.

An inadvertent release of hydrazine to the environment can be extremely hazardous due to the mutagenic nature of such chemical compounds, which can induce tumor growth in human beings years following even a low level exposure. Hydrazine compounds are classified as suspected human carcinogens and their permissible levels of exposure have been reduced to 10 parts per billion (ppb). A hydrazine spill remediation process, to be developed, should not only remediate the hydrazine, but also should not generate other hazardous materials. An in-situ processing method involving direct application of the treatment reagent or process to the spill is preferred.

An accident involving a transport trailer, for example, may spill four to five thousand gallons of the hydrazine fuel, whereas a catastrophic failure of a fuel storage vessel at a launch facility may release twenty thousand gallons or more of the propellant. A rail car derailment resulting in a hydrazine (i.e., commercial use) release occurred, for example, in Southern California on Jul. 28, 1991.

The U.S. Occupational Safety and Health Administration (OSHA), for example, requires the prevention of exposure to hydrazine and its derivatives at concentrations greater than one part per million (1.3 mg/m3). Hydrazine and hydrazine derivatives are readily combustible reducing agents that react violently with oxidizing agents and thus present a serious safety hazard. Hydrazine and hydrazine derivatives are well known components of liquid rocket fuels in conjunction with an oxidizing agent such as dinitrogen tetroxide. Thus, at facilities where liquid-fueled rockets are prepared for flight, there is a particular need to provide reliable and sensitive methods and systems for decontaminating objects such as fighter jets and maintenance equipment thereof, and exposed environments which can become contaminated with hydrazine. Ideally, such hydrazine remediation methods and systems should also have a limited, if negligible effect on the environment.

Examples of hydrazine neutralization techniques are known. One example of such a technique is disclosed in U.S. Pat. No. 4,804,527, entitled "Method and Composition for Safely Decomposing Hydrazine," which issued to Tatarchuk, et al. on Feb. 14, 1989. As described in U.S. Pat. No. 4,804,527, hydrazine can be safely rendered harmless by contacting it with a composition comprising cupric oxide on a porous support. Neutralization can be achieved by drawing the hydrazine into the pellet pores where a reduction reaction of cupric oxide takes place. The critical consideration is to avoid flashing or spontaneous thermal decomposition of the hydrazine. Heat of reaction is quenched by the heat capacity of the pellet and water dilution.

The conversion of hydrazine group compounds to stable organic compounds as a result of a reaction with a dicarbonyl-compound like ketoglutaric acid is described in the U.S. Patent Application Publication No. 2004/0024251 by Helvenston, et al. entitled "Methods and Systems for Hydrazine Remediation". In U.S. Patent Application Publication No. 2004/0024251, which is incorporated herein by reference, the conversion assists in the remediation of the hydrazine group compound from the object. The stable organic compound produced as a result of the reaction between the dicarbonyl-compound and hydrazine group compound can then be treated with a metal catalyst and hydrogen to produce glutamine or a derivative thereof. The compound then becomes a non-hazardous material. Such an approach is also described in U.S. Pat. No. 7,074,959, which issued to Helvenston, et al. on Jul. 11, 2006 and which is also incorporated herein by reference in its entirety.

The present invention is a novel application of the reaction between hydrazine and a dicarbonyl compound for remediating hydrazine from contaminated air.

BRIEF SUMMARY

The following summary of the invention is provided to facilitate an understanding of some of the innovative features unique to the present invention and is not intended to be a full description. A full appreciation of the various aspects of the invention can be gained by taking the entire specification, claims, drawings, and abstract as a whole.

It is, therefore, one aspect of the present invention to provide for a system and method for remediating hydrazine, 1,1-dimethylhydrazine, and/or monomethyl-hydrazine from contaminated air.

It is, therefore, another aspect of the present invention to provide for a system and method to remediate spills of hydrazine, 1,1-dimethylhydrazine, and/or monomethyl-hydrazine.

The aforementioned aspects of the invention and other objectives and advantages can now be achieved as described herein. In one embodiment, a method and system are disclosed for remediating hydrazine from hydrazine contaminated air as illustrated in the form of a container into which the contaminated air flows and encounters with an absorbent material (e.g., filters/pads/wipes) treated with a dicarbonyl compound. Note that as utilized herein the term "hydrazine" can refer simply to hydrazine and/or, 1,1-dimethylhydrazine, and/or monomethyl-hydrazine. The air can be drawn into the container by a fan or vacuum. The fan may be located on the "clean" side of the container or at other appropriate locations about the container (e.g., left side, right side, top, bottom, etc). Air exiting the container is free of hydrazine. The container includes an inflow port and an outflow port coupled to the fan. The pads or wipes, for example, can also be used independently of the container as an absorbent for remediating hydrazine spills. In its operational form, the dicarbonyl compound may be present on or in the absorbent material in a dry form.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION OF THE INVENTION

Figure 1:
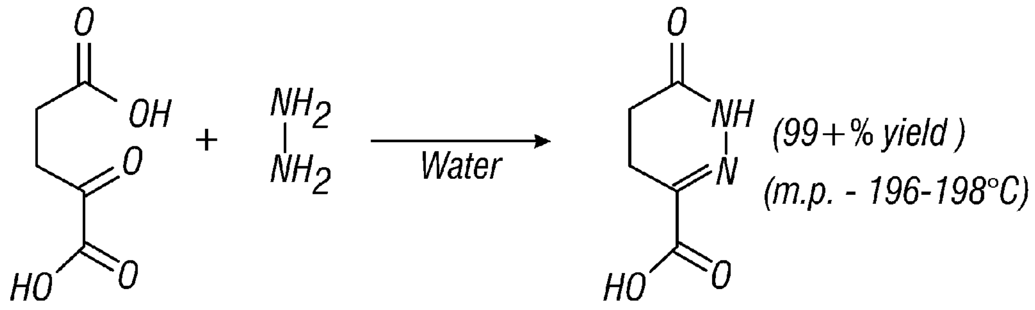
FIG. 1 illustrates a scheme indicative of the reaction of hydrazine (Hz) with 2-ketoglutaric acid (2 KG)

The particular values and configurations discussed in these non-limiting examples can be varied and are cited merely to illustrate at least one embodiment of the present invention and are not intended to limit the scope of the invention.

The disclosed embodiments stem from the examination of several classes of compounds that quantitatively react with hydrazine to form stable organic products. The reaction of 2-ketoglutaric acid with hydrazine reacts to provide a greater than 99% yield of 6-oxo-1,4,5,6-tetrahydro-pyridazine-3-carbonic acid (PCA) based on hydrazine as the limiting reagent. It has been found that this compound allows for the facile remediation of hydrazine under a variety of conditions. The focus of the disclosed embodiments concerns the use of 2-ketoglutaric acid or other dicarbonyl compounds for the remediation of hydrazine.

Several classes of organic compounds have been examined by the present inventors. Such compounds react rapidly and quantitatively with hydrazine to form stable organic products. The solid-state reaction (on a milligram scale) of a hydrazine complex with 2-ketoglutaric acid (2 KG) has been demonstrated. Such a reaction can produce 6-oxo-1,4,5,6-tetrahydro-pyridazine-3-carbonic acid in near quantitative yield (98%) based on hydrazine as the limiting reagent. The present inventors have found that this compound allows for the facile remediation of hydrazine under a variety of conditions. The present inventors have also ascertained that 2 KG has an excellent potential to reduce the hazards associated with the handling and storage of hydrazine fuels. The present inventors have implemented extensive work on the reaction between Hz and 2 KG. Such a reaction has been found to be very effective at converting technical grade hydrazine and to less than ppm levels (none detected by Draeger Tube measurement and other methods). The remediation of hydrazine occurs in less than one hour without the evolution of excessive heat.

An examination of the use of various keto-acids (e.g., such as 2-ketoglutaric acid and other dicarbonyl compounds) for the production of a hydrazine filter has been performed. Such an examination relates to the development of the hydrazine air filter, which is disclosed in greater detail herein and is based on determining the optimal solid support (e.g., carbon, etc.) and keto-acid to maximize filter efficiency, along with the development of methods for the extraction of the hydrazine adduct.

The inventors have found that inexpensive solid supports offer a safer option for efficient use of the keto-acid. An air filtration system passes gas over a solid reactant, for example; it is reasonable to expect that reagent near the surface reacts readily, while interior portions react slowly. The inventors have demonstrated that this is an effective approach for the remediation of hydrazine (e.g., hydrazine, 1,1-dimethylhydrazine, and/or monomethyl-hydrazine). However, such a configuration can lead to poor utilization of the reagent. Thus, attempts at coating a variety of glass, ceramic, and carbon supports of different particle size were undertaken. Aqueous and methanolic solutions of the keto-acid were deposited onto substrates by vacuum evaporation of solvents while continuously rotating the container. In most cases this process resulted in clumped aggregates rather than coated particles, even from relatively dilute solutions of keto-acid. However, sand appears to coat uniformly based on appearance and microscopic observations. Smaller particles of silica and glass helices clumped or gave poor uniformity of deposition. Larger grains or gravel provide too little surface area relative to the large mass they bring. Consequently, sand coated with different loadings of reagent was pursued further and the remediation results are described later herein.

Attempts to coat ceramic saddles by spraying the pieces with concentrated solutions of keto-acid and allowing for air drying afforded poor uniformity of coating. Solvent appeared to leach towards the most exposed sites where most of the evaporation of solvent occurred. Ceramic saddles afford high surface area relative to their mass and have higher airflow capacity. The saddles are well suited to air filtration and are being explored with a solution based counter-flow apparatus of similar design to the full scale air filtration apparatus NASA, for example, currently uses at launch sites.

FIG. 1 illustrates a scheme indicative of the reaction of hydrazine (Hz) with 2-ketoglutaric acid. The chemical formulation depicted in scheme 10 is based on the use of 2-ketoglutaric acid or other dicarbonyl compounds for the remediation of hydrazine, in accordance with an embodiment.

Figure 2:
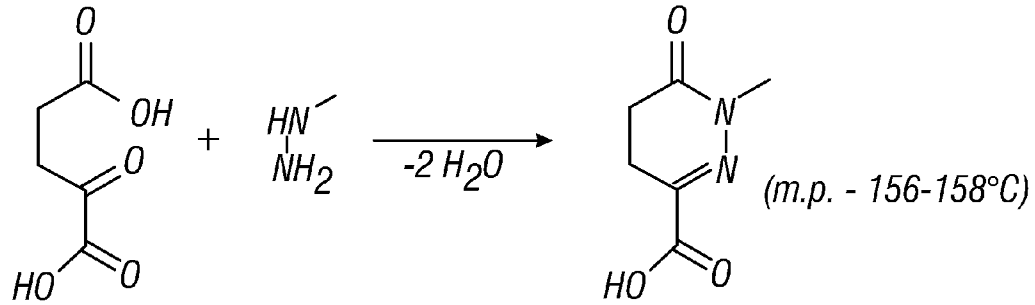
FIG. 2 illustrates a scheme outlining the reaction of monomethyl-hydrazine (MMH), with 2-ketoglutraric acid, in accordance with an embodiment.

FIG. 2 illustrates a scheme 20 outlining the reaction of monomethyl-hydrazine (MMH), with 2-ketoglutraric acid, in accordance with an embodiment. The product of the reaction of scheme 20 is also a high melting stable organic molecule.

A variety of pyridazine ring systems have been used extensively for a variety of medical applications. These include pharmaceuticals for heart disease, HIV, Alzheimer's disease, antidepressants, and even cognitive enhancement drugs. The MSDS (HMIS rating) hazard classification and the DOT classifications for the hydrazine reagents and the compounds described above appear in Table 1 below:

TABLE 1

Shows the HMIS ratings (Scale 0-4) and DOT Dangerous Goods Ratings (8 = Corrosive)
MSDS - Hazards Identification (HMIS Ratings) and Transportation (DOT) Regulations

| Compound | Health (Acute Effects) | Flammability | Reactivity | Transportation Regulations |
|---|---|---|---|---|
| Hydrazine | 3 | 3 | 3 | 8 |
| Monomethyl Hydrazine | 3 | 3 | 3 | 8 |
| Dimethyl Hydrazine | 3 | 3 | 3 | 8 |
| 2-Ketoglutaric acid | 1 | 1 | 0 | None |
| 6-Oxo-1,4,5,6-tetrahydropyridazin-3-carcontainerylic acid (PCA) | 1 | 1 | 1 | None |
| Glutamine | 1 | 1 | 0 | None |
| Methyl glutamic acid | 1 | 1 | 1 | None |
| Glutamic acid | 1 | 1 | 1 | None |
| Pyroglutamic acid | 2 | 1 | 0 | None |

Hydrazine group compounds hydrazine (Hz), monomethylhydrazine (MMH), and 1,1-dimethylhydrazine (UDMH) are widely used as fuels (in rocket propulsion systems and fighter jets), corrosion inhibitors (nuclear industry), catalysts, emulsifiers, or dyes. It also is a common precursor in the synthesis of a number of polymers, plasticizers, and pesticides. Recently, a variety of medicinal drugs have incorporated the hydrazine molecule. The inventors are currently examining compounds that will react with hydrazine rapidly and quantitatively.

Figure 3:
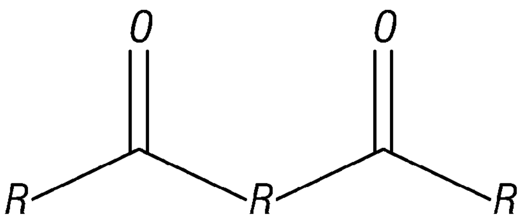
FIG. 3 illustrates general structural formulas for dicarbonyl compounds, which can be utilized in accordance with varying embodiments.
Figure 3:
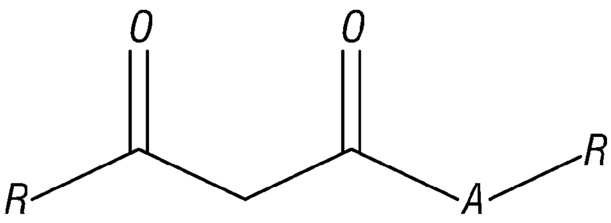
Figure 3:
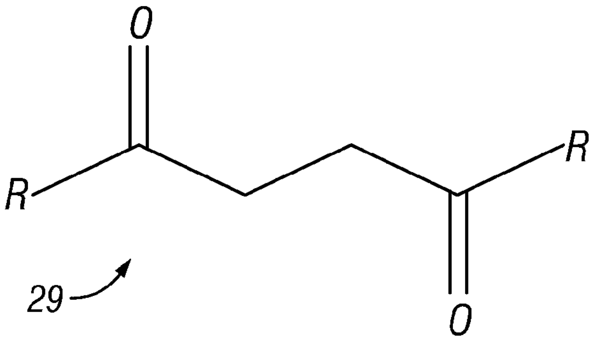
Figure 3:
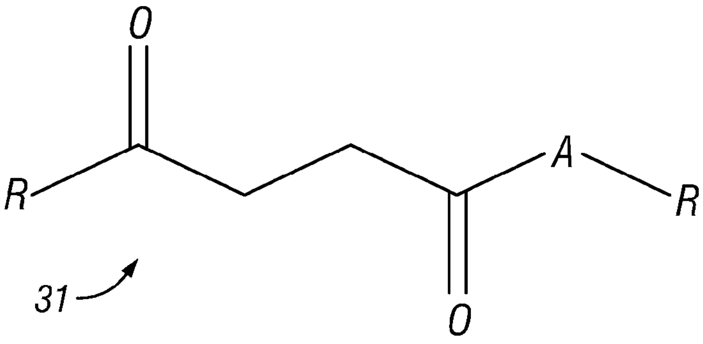

FIG. 3 illustrates general structural formulas for dicarbonyl compounds as shown by chemical schemes 25, 27, 29, and 31, respectively, I, II, III and IV. I and II are examples of beta-dicarbonyl compounds, while III and IV are gamma-dicarbonyl compounds. More remote dicarbonyl compounds may also be used. Examples of these compounds are acetoacetone, propanedial, ethyl acetoacetate, levulinic acid, ethyl levulinate, and 1,3-diphenylpropane-1,3-dione. Other carbonyl-like functional groups can also undergo a comparable reaction with hydrazine and are included as a part of the definition of dicarbonyl compounds utilized herein. Acetoacetonitrile is an example of such a compound.

Figure 4:
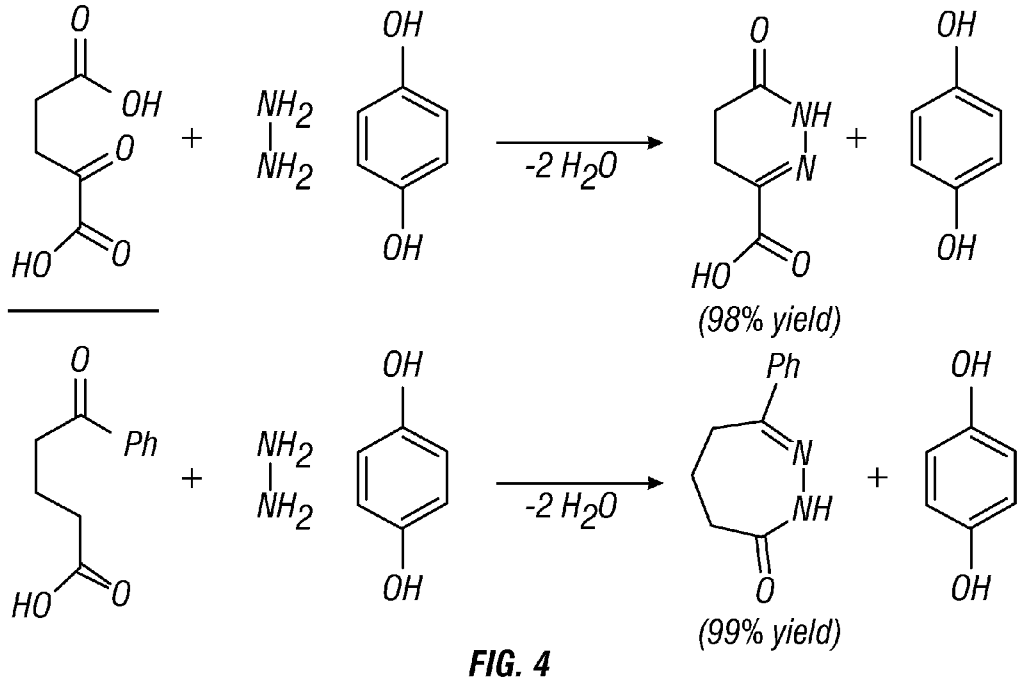
FIG. 4 illustrates examples of the reaction between a keto-acid and a complex of hydrazine, in accordance with an embodiment.

Two classes of compounds that were examined are keto-acids and keto-esters. FIG. 4 illustrates a schematic diagram depicting examples of the reaction between a keto-acid and a complex of hydrazine. In each case the solid compounds were ball milled at room temperature in a ratio of 2:1 (keto-acid to hydrazine complex) and a near quantitative yield was obtained. The 6-oxo-1,4,5,6-tetrahydro-pyridazine-3-carbonic acid (CAS#27372-38-9) formed from the reaction of 2 KG and the hydrazine complex is a high melting solid (m.p. 196-198° C.). The MSDS for this compound does not show any transportation hazards and is not listed on the TSCA list of hazardous or regulated compounds. Therefore, the waste stream from this process (if we choose to dispose of it at this time) would no longer be a hazard. When hydrazine is treated with an aqueous solution of 2 KG, the 6-oxo-1,4,5,6-tetrahydro-pyridazine-3-carbonic acid (PCA) is immediately formed. PCA precipitates and can be recovered as a pure compound.

Figure 5:
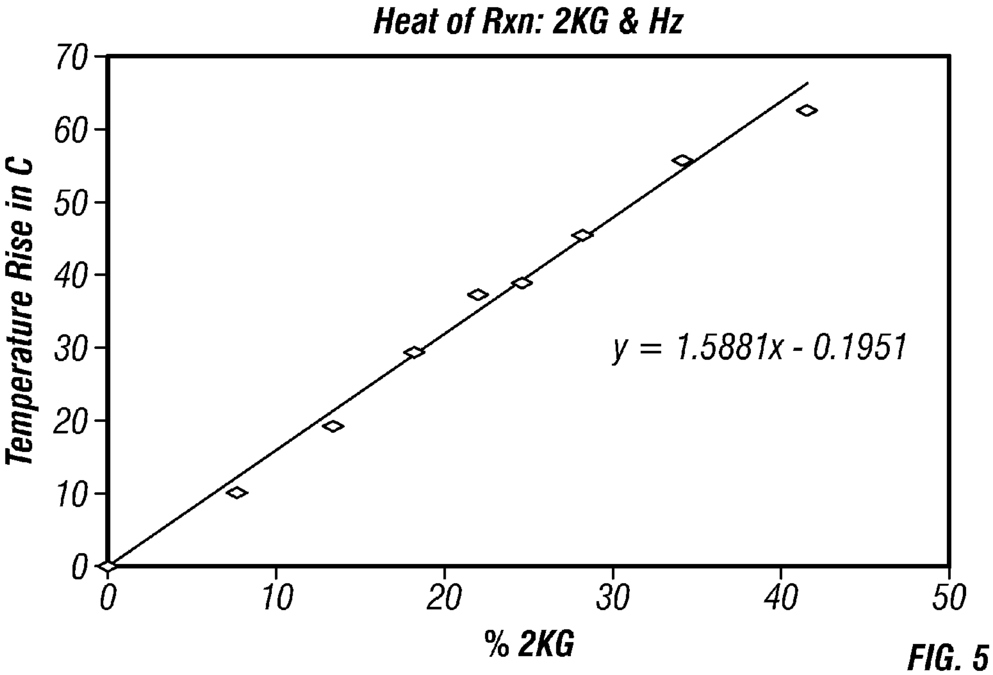
FIG. 5 illustrates a graph depicting the temperature increase from the reaction between hydrazine and solutions varying concentrations of 2 KG, in accordance with an embodiment.

The amount of heat that is produced from this reaction is dependent on the concentration of 2 KG. FIG. 5 illustrates a graph depicting the temperature increase from the reaction between hydrazine and solutions varying concentrations of 2 KG. The data in the graph of FIG. 5 demonstrates the relationship between concentration and heat produced by the reaction. For example, 15 grams of 2 KG were dissolved with 75 mL of water, then 7 mL (1.1 equivalents) of hydrazine monohydrate were added for the point at 20%. The MMH reaction with 2 KG also produces a 3-pyridazinecarcontainerylic acid, 1,4,5,6-tetrahydro-1-methyl-6-oxo-cyclic structure. It has a melting point of 156-158° C.

Figure 6:
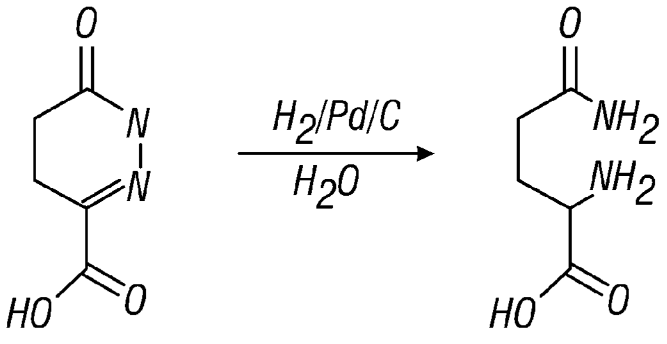
FIG. 6 illustrates a scheme in which the cyclic compounds can be treated with hydrogen gas over a palladium catalyst in water to produce D,L-glutamine.
Figure 7:
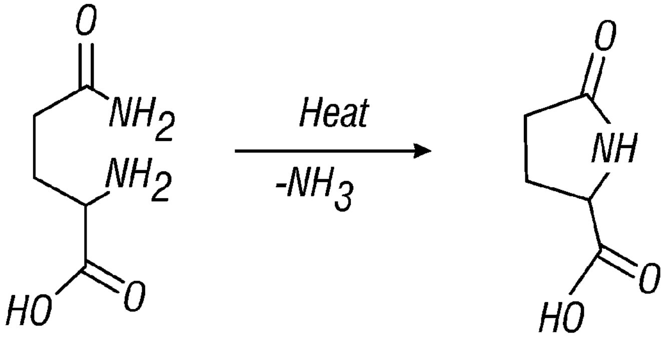
FIG. 7 illustrates a scheme in which the compound can be treated with heat to produce the sample compound D, L-proline, 5-oxo-, in accordance with an embodiment.
Figure 8:
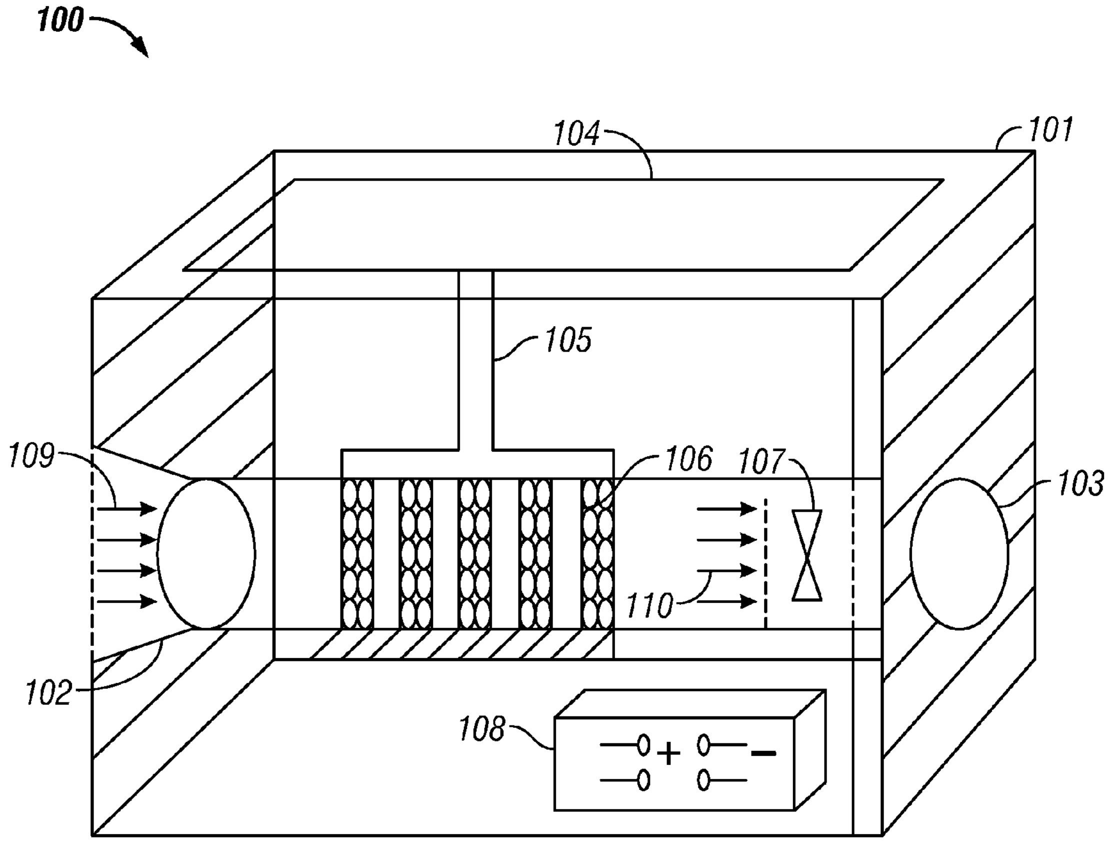
FIG. 8 illustrates a pictorial diagram of a system for remediating hydrazine from contaminated air, in accordance with an embodiment.

An extraction method was not necessary because the 3-pyridazinecarcontainerylic acid, 1,4,5,6-tetrahydro-1-methyl-6-oxo- was a solid which precipitated from the reaction. The cyclic compounds can be treated with hydrogen gas over a palladium catalyst in water to produce D,L-glutamine as illustrated in the scheme 60 depicted in FIG. 6. The compound can then be treated with base and heated to produce the sample compound D,L-proline, 5-oxo- as shown in scheme 70 depicted in FIG. 7. Additional work has yielded an air filtration system that allows for the safe and efficient removal of hydrazine. FIG. 8 illustrates an example of such an air filtration system. The ambient air in a workspace may be drawn through the filtration system 100 depicted in FIG. 8, which provides a safer work environment.

FIG. 8 therefore illustrates a schematic diagram of a system 100 implemented in the context of a container 101 for the remediation of hydrazine from contaminated air, in accordance with an embodiment. Preferably, the container 101 is rectangular in shape and is made of heat resistant materials like metal, aluminum, carbon, or plastic. Although the external appearance of the container 101 is preferably rectangular in shape it can be appreciated that the container 101 can be implemented as a square, rectangular, circular, round, oval, or other shape (e.g., custom shaped), depending upon design considerations. Thus, the use of a rectangular shape is not considered a limiting feature of the embodiments, but is described herein for general illustrative purposes only. System 100 includes inlet port 102 and an outlet port 103, which respectively permits air to enter into and go out of the container 101.

The container 101 includes a removable lid 104 thereon to which a water dripping mechanism 105 may be attached. The water dripping mechanism 105 can be utilized, for example, to spray or drip water onto the absorbent material 106 arranged within the container 101. Note that in one embodiment, the absorbent material 106 may be provided as a wipe or wipes. In another embodiment, such absorbent material 106 may be implemented as one or more absorbing pads, filters, wipes, or other such appropriate media. A fan or vacuum pump 107 can be attached near the side of the outlet port 103 and can be used to draw air into the container 101.

If in the form of a pad or filter, for example, the absorbent material 106 may be formed from appropriate materials within containment net. Examples of such materials include excelsior (wood wool), aspen wood fiber, etc. Other potential materials include plastics and melamine paper. The thickness of the padding media may play a part in the decontamination efficiency, allowing for longer air contact. For example, an eight-inch-thick pad with its increased surface area may be more efficient than a one-inch pad.

The absorbent material 106 may be saturated with a solution (e.g., aqueous or dry) of a dicarbonyl compound such as, for example, ketoglutaric acid. In some embodiments, the dicarbonyl compound preferably may constitute a dry powder after treatment of the absorbent material. A power supply 108 may also be incorporated within and/or integrated with the container 101. As indicated in the configuration depicted in FIG. 8, contaminated air 109 may enter the container 101 through the inlet 102 and pure air 110 leaves the container through the outlet 103. The absorbent material 106 is removable and can be replaced when stable organic compounds formed by the reaction between hydrazine and the dicarbonyl compound accumulated thereon.

Figure 9:
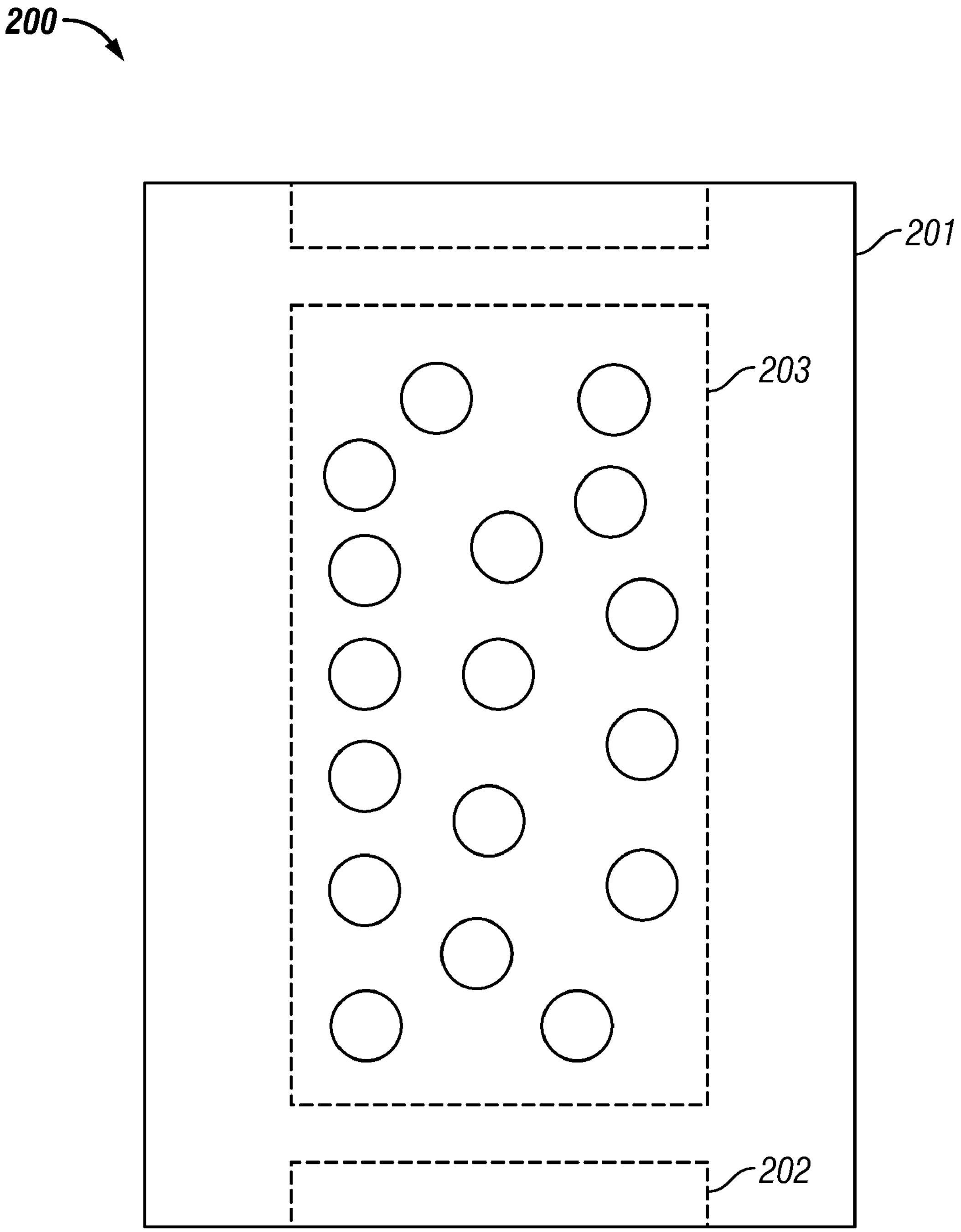
FIG. 9 illustrates a diagrammatic representation of the cross section of absorbing material (e.g., pads, wipes or filters), in accordance with an embodiment.

FIG. 9 depicts a cross-sectional of the absorbent material 106 depicted in FIG. 8, in accordance with an embodiment. The material 106 (e.g., a pad or wipe) generally includes a porous surface cover 201 which may surround a shape, including an inert absorbent interior component which, in turn, surrounds an absorbent interior core comprising a dicarbonyl compound such as ketoglutaric acid that reacts with hydrazine present in air or any liquid spill, such that the spill or air components are neutralized within the absorbent material 106.

In accordance with one embodiment, the absorbent material 106 can include a porous outer fabric surface covering that draws hydrazine from a chemical spill on a substrate or present in air to the absorbing pad. The surface covering material may be desirably a chemically resistant cloth or cloth-like material which will shape and maintain the integrity of the pad while containing the inner components and absorbed liquid during use.

An absorbent component 202 can be disposed inside the outer fabric bag with an absorbent interior or core 203. The absorbent interior core of the pad is generally disposed or embedded within the absorbent component and can include dicarbonyl compounds (e.g., aqueous solution or dry solution) such as, for example, ketoglutaric acid for reacting with hydrazine in air or in the liquid spill.

In use, the spilled hydrazine can be diluted with water before the pad or wipe is applied to clean up the spill. The water in the aqueous solution, for example, assists in the chemical reaction by allowing the hydrazine to gradually migrate to the absorbent interior where the aqueous hydrazine is converted into a stable organic compound by reacting with the dicarbonyl compound in the pad. Water also assists in controlling the heat formed during the reaction. The amount of water to be added is not strictly defined and can be varied by those skilled in the art.

It can be appreciated that system 100 is also capable of remediating hydrazine without the absorbent material 106 as described above. For example, a "dry" implementation of system 100 can be configured, in accordance with an alternative embodiment, in which an aerosol is employed in place of the absorbent material 106, wherein such an aerosol may contain an aqueous or dry powder composed of, for example, ketoglutaric acid. See, for example, FIG. 11, which illustrates such an alternative embodiment.

Figure 10:
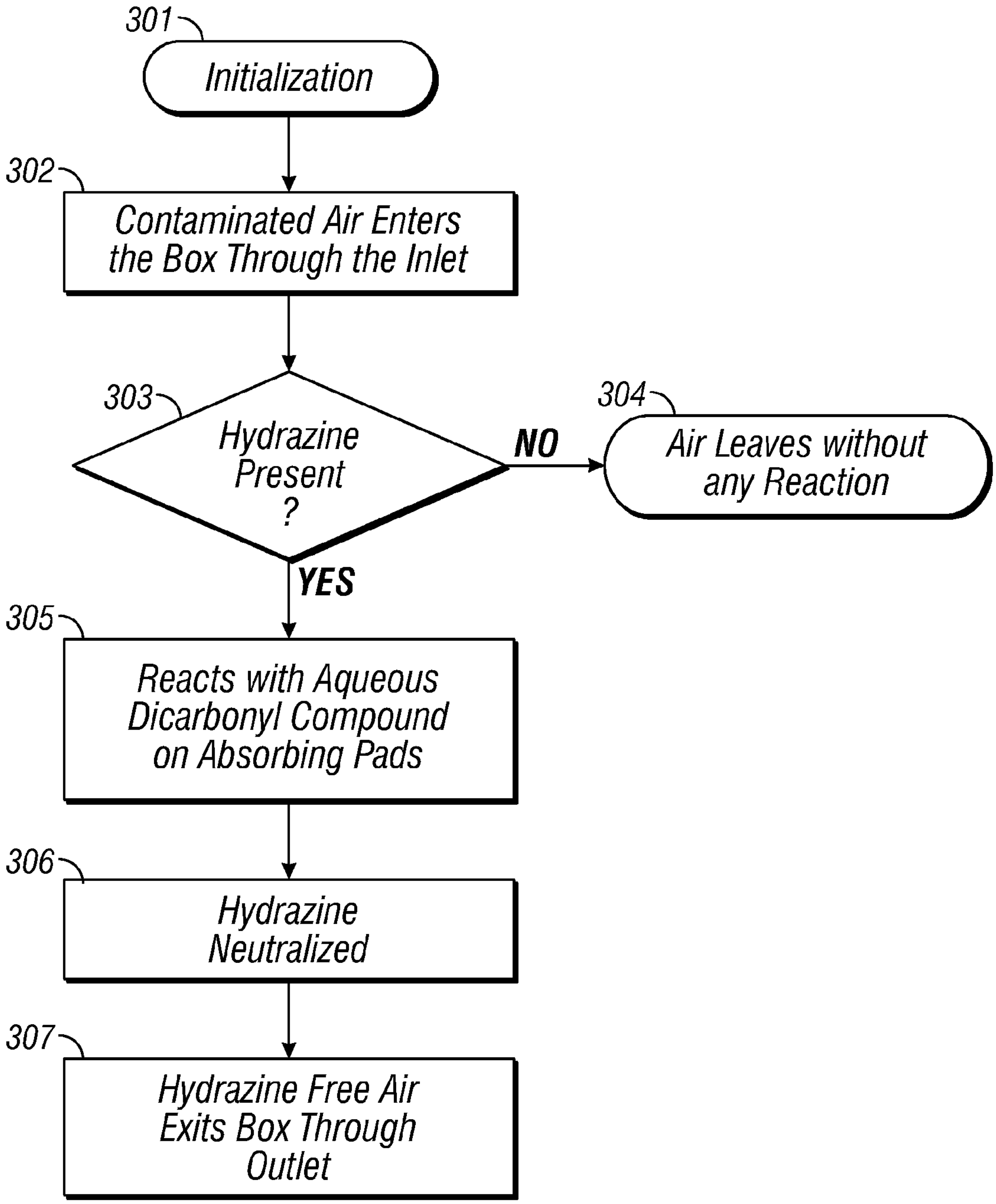
FIG. 10 illustrates a flow chart of operations depicting the operation of the system depicted in FIG. 8 for the remediation of hydrazine from contaminated air, in accordance with an embodiment.

FIG. 10 illustrates a high-level flow chart of logical operational steps, which can be implemented in accordance with a preferred embodiment. When the process is initialized as illustrated at block 301, air enters through the inlet port 101 as indicated at block 302. If no hydrazine is present in the contaminated air, it passes out of the container 101 without any reaction, as depicted at block 304. If, however, hydrazine is present as indicated at block 303, it reacts with the solution (e.g., aqueous or dry) of dicarbonyl compound located on the absorbent material 106 as depicted at block 305. As a result, hydrazine is neutralized, as indicated at block 306, the contaminated air becomes free of hydrazine as depicted at block 307, and exits the container or box 101 through the outlet port 103. Thus, purified air exits via the outlet port 103 as described at block 307.

Figure 11:
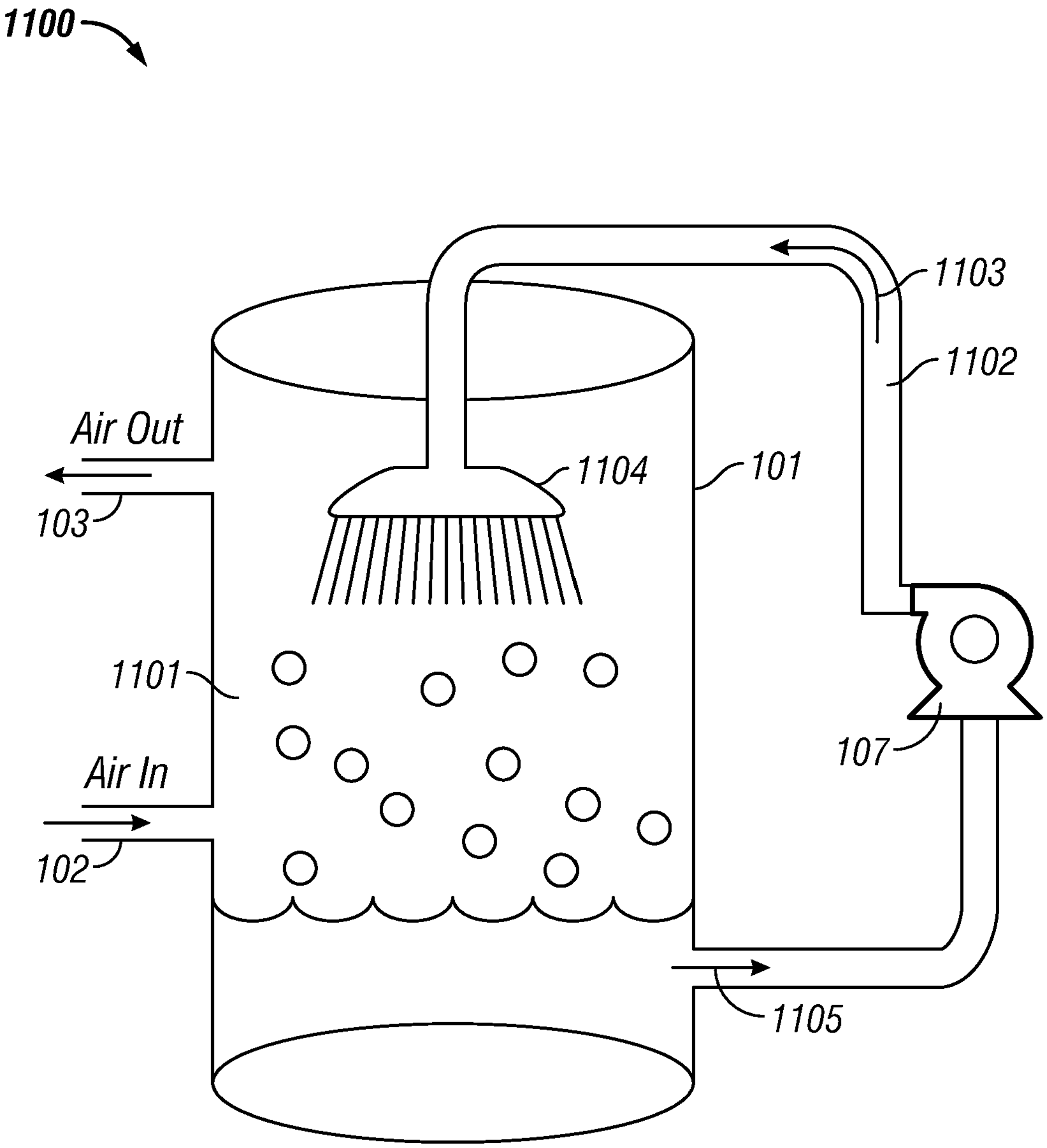
FIG. 11 illustrates a pictorial diagram of a system for remediating hydrazine from contaminated air, wherein the system includes a cylindrical container, in accordance with an embodiment.

FIG. 11 illustrates a pictorial diagram of a system 1100 for remediating hydrazine from contaminated air, wherein the system 1100 includes a cylindrical container 101, in accordance with an embodiment. Note that the system 1100 depicted in FIG. 11 illustrates an alternative version of the embodiment of system 800 depicted in FIG. 8. The container 101 illustrated in FIG. 8 is generally square or rectangular in shape, whereas the container 101 as depicted in FIG. 11 is cylindrical shape. The container 101 depicted in FIG. 11 functions as a reactor and generally includes an inlet port 102 and an output port 103. Hydrazine contaminated air enters the container 101 through the inlet port 102. Decontaminated air exits via the outlet port 103. Liquid travels as indicated by arrow 1103 through a channel 1102 from the bottom of the container 101 and can exit through a spray nozzle 1104 connected to the channel 1102. A pump 107 generally assists in moving fluid from the container 101 through the channel 1102 (e.g., a hose or tubing) and toward the top of the container 101 where it exits through the spray nozzle 1104.

System 1100 thus can function as a gas scrubbing system. Contaminated gas flows into the container or reactor 101 through the inlet port or orifice 102 upward through the reactor 101 and out the outlet port or orifice 103. A solution of dicarbonyl compound is thus re-circulated through the reactor 101. The solution is sprayed from the spray nozzle 1104 over a stationary solid support 1101, over which it drains down to the bottom of the reactor or container 101 and is sucked out by pump 107 through an orifice 1105. The stationary solid support material 1101 may be, for example, plastic, metal, glass, ceramic, or other solids, and may possess various shapes either of regular structures such as saddles or irregular shapes such as broken glass.

The disclosed system and methodology offer a number of advantages and is particularly useful to those industries where hydrazine is utilized and potentially leads to contamination. The electrical generating industry, for example, is one area where hydrazine contamination presents a significant possibility. As such, the approach disclosed herein would be particularly useful in this environment.

In the aerospace industry, for example, emergency hydraulic and electric power may be provided by a particular turbine engine. When the hydrazine and water mixture is released and passes across a catalyst of iridium, it spontaneously ignites, creating hot expanding gases which drive the turbine. The power created is transmitted through a gearbox to drive an electrical generator and hydraulic pump. The hydrazine is contained in a sealed, nitrogen charged accumulator. When the system is armed, the hydrazine is released whenever the engine-driven generators go off-line, or if all engine-driven hydraulic pumps fail. Such hydrazine, when released, may pose a hazard to human health.

Electrical fuel cell applications are another example where hydrazine contamination may come into effect. For example, some fuel cell technology may eliminate the need for platinum, a precious metal that has been an essential material in the electrode catalyst in conventional fuel cells for automobiles. However, such technology also fixes hydrazine hydrate inside the fuel tank to ensure its safe use as a fuel, resulting in no tailpipe CO2 emissions at all. Thus, if hydrogen fuel cell technology, in particular, is widely adopted in the future, the potential for hydrazine leakage is possible.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. A system for the remediation of air contaminated with hydrazine, said system comprising:

a container with an inlet through which air contaminated with hydrazine enters said container;

an outlet through which decontaminated air passes out of said container; and at least one absorbent material located within said container, said at least one absorbent material comprising an absorbent medium having dicarbonyl compound, wherein said air contaminated with hydrazine reacts with said dicarbonyl compound to neutralize and convert said air contaminated with hydrazine into decontaminated air comprising a stable organic compound that exits said container through said outlet.

2. The system of claim 1 wherein said dicarbonyl compound comprises ketoglutaric acid.

3. The system of claim 1 wherein said dicarbonyl compound comprises a beta-dicarbonyl compound.

4. The system of claim 1 wherein said dicarbonyl compound comprises a gamma-dicarbonyl compound.

5. The system of claim 1 wherein said dicarbonyl compound comprises a remote dicarbonyl compound.

6. The system of claim 5 wherein said remote dicarbonyl compound comprises acetoacetone.

7. The system of claim 5 wherein said remote dicarbonyl compound comprises propanedial.

8. The system of claim 5 wherein said remote dicarbonyl compound comprises ethyl acetoacetate.

9. The system of claim 5 wherein said remote dicarbonyl compound comprises levulinic acid.

10. The system of claim 5 wherein said remote dicarbonyl compound comprises ethyl levulinate.

11. The system of claim 5 wherein said remote dicarbonyl compound comprises 1,3-diphenylpropane-1,3-dione.

12. The system of claim 1 wherein said dicarbonyl compound comprises a compound selected from a carbonyl-like functional group.

13. The system of claim 12 wherein said dicarbonyl compound selected from a carbonyl-like functional group comprises acetoacetonitrile.

14. The system of claim 1 wherein said dicarbonyl compound comprises a dry powder.

15. The system of claim 1 wherein said dicarbonyl compound comprises an aerosol.

16. The system of claim 1 wherein said absorbent medium comprises an aqueous absorbent medium.

17. The system of claim 1 wherein said container comprises a natural material.

18. The system of claim 1 wherein said container comprises metal.

19. The system of claim 1 wherein said container comprises glass.

20. The system of claim 1 wherein said container comprises a synthetic material.

21. The system of claim 1 wherein said container comprises a heat resistant material.

22. The system of claim 1 wherein said at least one absorbent material permits said air contaminated with hydrazine to pass through said at least one absorbent material.

23. The system of claim 22 wherein said at least one absorbent material comprises a pad.

24. The system of claim 22 wherein said at least one absorbent material comprises a fibrous material.

25. The system of claim 22 wherein said at least one absorbent material comprises a granular material.

26. The system of claim 1 further comprising:

a drip mechanism connected to said container, said drip mechanism configured to deliver liquid to said at least one absorbent material within said container to control heat produced during a chemical reaction within said container; and a removable lid coupled to said container and said drip mechanism.

27. The system of claim 1 further comprising a fan located approximate to said outlet of said container, wherein said fan draws said decontaminated air out of said container through said outlet.

28. The system of claim 1 further comprising a fan located approximate to said inlet of said container, wherein said fan draws said air contaminated with hydrazine into said container through said inlet.

29. The system of claim 1 further comprising a suction mechanism located approximate to said outlet of said container, wherein said suction mechanism draws said decontaminated air out of said container through said outlet.

30. The system of claim 1 further comprising a suction mechanism located approximate to said inlet of said container, wherein said suction mechanism draws said air contaminated with hydrazine into said container through said inlet.

31. A system for the remediation of air contaminated with hydrazine, said system comprising:

a container with an inlet through which air contaminated with hydrazine enters said container;

an outlet through which decontaminated air passes out of said container; and at least one absorbent material located within said container, said at least one absorbent material comprising an absorbent medium to which a dicarbonyl compound is previously applied, said dicarbonyl compound comprising a dry powder composed of ketoglutaric acid, wherein said air contaminated with hydrazine reacts with said dicarbonyl compound to neutralize and convert said air contaminated with hydrazine into decontaminated air comprising a stable organic compound that exits said container through said outlet and wherein said at least one absorbent material permits said air contaminated with hydrazine to pass through said at least one absorbent material.

32. The system of claim 31 wherein said container comprises container walls comprising at least one material selected from the following group of materials: metal, glass, and a synthetic material.

33. A system for the remediation of air contaminated with hydrazine, said system comprising:

a container with an inlet through which air contaminated with hydrazine enters said container;

an outlet through which decontaminated air passes out of said container;

at least one absorbent material located within said container, said at least one absorbent material comprising an aqueous absorbent medium to which a dicarbonyl compound is previously applied, said dicarbonyl compound comprising a dry powder composed of ketoglutaric acid;

a first suction mechanism located approximate to said outlet of said container, wherein said suction mechanism draws said decontaminated air out of said container through said outlet; and a second suction mechanism located approximate to said inlet of said container, wherein said suction mechanism draws said air contaminated with hydrazine into said container through said inlet, wherein said air contaminated with hydrazine reacts with said dicarbonyl compound to neutralize and convert said air contaminated with hydrazine into decontaminated air comprising a stable organic compound that exits said container through said outlet and wherein said at least one absorbent material permits said air contaminated with hydrazine to pass through said at least one absorbent material.

34. The system of claim 33 further comprising:

a drip mechanism connected to said container, said drip mechanism configured to deliver liquid to said at least one absorbent material within said container to control heat produced during a chemical reaction within said container; and a removable lid coupled to said container and said drip mechanism.

35. The system of claim 33 wherein said at least one absorbent material comprises a pad or a wipe.

* * * * *